US012201810B2

(12) United States Patent
Hamon et al.

(10) Patent No.: US 12,201,810 B2
(45) Date of Patent: Jan. 21, 2025

(54) SPLINT FOR AN INFANT

(71) Applicant: MWDESIGN LIMITED, Hamilton (NZ)

(72) Inventors: Jack Hamon, Hamilton (NZ); Michael Bryan Williams, Hamilton (NZ)

(73) Assignee: MWDESIGN LIMITED, Hamilton (NZ)

( * ) Notice: Subject to any disclaimer, the term of this patent is extended or adjusted under 35 U.S.C. 154(b) by 903 days.

(21) Appl. No.: 17/054,649

(22) PCT Filed: May 10, 2019

(86) PCT No.: PCT/NZ2019/050052
§ 371 (c)(1),
(2) Date: Nov. 11, 2020

(87) PCT Pub. No.: WO2019/216776
PCT Pub. Date: Nov. 14, 2019

(65) Prior Publication Data
US 2021/0077715 A1 Mar. 18, 2021

(30) Foreign Application Priority Data
May 11, 2018 (NZ) ....................................... 742444

(51) Int. Cl.
*A61M 5/158* (2006.01)
*A61F 5/058* (2006.01)
(52) U.S. Cl.
CPC ........... *A61M 5/158* (2013.01); *A61F 5/0585* (2013.01); *A61F 5/05866* (2013.01);
(Continued)
(58) Field of Classification Search
CPC .......... A61M 5/158; A61M 2005/1586; A61M 2205/0238; A61M 2207/10;
(Continued)

(56) References Cited

U.S. PATENT DOCUMENTS 2,809,042 A * 10/1957 Wasley .............. A63B 69/3608
473/214
3,942,525 A * 3/1976 Dragan ................. A61F 5/0118
473/62
(Continued)

FOREIGN PATENT DOCUMENTS

WO  WO-2011030226 A2 * 3/2011 ............ A61F 5/0118
WO  WO-2014181164 A1 * 11/2014 ............. A61L 29/00
WO  WO-2016123652 A1 * 8/2016 ......... A61F 5/05825

OTHER PUBLICATIONS

PRIMACARE Medical supplies 2014 product brochure, PDF downloaded from www.primacaremedical.com Nov. 11, 2019.
(Continued)

*Primary Examiner* — Tarla R Patel
(74) *Attorney, Agent, or Firm* — Piloff Passino & Cosenza LLP; Martin J. Cosenza

(57) ABSTRACT

The invention relates to a splint for an infant. It has a body including an insert of a malleable material, wherein the body has a longitudinal axis, a first arm extending from an edge of the body in a plane substantially perpendicular to the longitudinal axis; and a second arm, spaced apart from the first arm, extending from the edge of the body in a plane substantially perpendicular to the longitudinal axis. The arms wrap around the limb of the infant and provide a surface for using medical tape or the like, thus avoiding the need for the tape to come into contact with the skin of the infant. In addition, the malleable insert allows the splint to be deformed and hold its shape if the splint is to be used on a joint of the limb.

20 Claims, 6 Drawing Sheets

(52) U.S. Cl.
CPC . *A61F 5/05875* (2013.01); *A61M 2005/1586* (2013.01); *A61M 2205/0238* (2013.01); *A61M 2207/10* (2013.01); *A61M 2240/00* (2013.01)

(58) Field of Classification Search
CPC ...... A61M 2240/00; A61M 2025/0206; A61M 2025/0213; A61M 25/02; A61M 2025/024; A61M 2025/0253; A61M 2025/026; A61F 5/0585; A61F 5/05866; A61F 5/05875; A61F 5/05858
See application file for complete search history.

(56) References Cited

U.S. PATENT DOCUMENTS

| | | | | |
|---|---|---|---|---|
| 4,161,175 | A * | 7/1979 | Bentele | B32B 3/28 |
| | | | | 602/6 |
| 4,502,477 | A * | 3/1985 | Lewis | A61M 25/02 |
| | | | | 128/DIG. 6 |
| 4,600,191 | A * | 7/1986 | Agius | A63B 69/0046 |
| | | | | 473/214 |
| 4,798,199 | A * | 1/1989 | Hubbard | A61M 25/02 |
| | | | | 128/845 |
| 4,945,925 | A * | 8/1990 | Garcia | A61F 5/05825 |
| | | | | 128/877 |
| 5,845,643 | A * | 12/1998 | Vergano | A61F 5/05866 |
| | | | | 128/877 |
| 7,402,149 | B1 | 7/2008 | Garelick et al. | |
| 8,123,681 | B2 * | 2/2012 | Schaeffer | A61M 25/02 |
| | | | | 600/179 |
| 2004/0225241 | A1 * | 11/2004 | Scheinberg | A61F 5/05866 |
| | | | | 602/5 |
| 2011/0066095 | A1 | 3/2011 | Price et al. | |
| 2014/0060547 | A1 * | 3/2014 | Vallino | A61F 5/05858 |
| | | | | 128/845 |
| 2016/0067080 | A1 * | 3/2016 | Sanders | A61G 13/1235 |
| | | | | 128/845 |
| 2016/0106958 | A1 | 4/2016 | Price | |
| 2016/0317785 | A1 * | 11/2016 | Wilborn | A61F 15/008 |

OTHER PUBLICATIONS

International Search Report & Written Opinion for PCT/NZ2019/050052, mailed Aug. 20, 2019.
International Preliminary Report on Patentability for PCT/NZ2019/050052, mailed Jun. 16, 2020.

* cited by examiner

SPLINT FOR AN INFANT

STATEMENT OF CORRESPONDING APPLICATIONS

This application is based on the provisional specification filed in relation to New Zealand Patent Application No. 742444, the entire contents of which are incorporated herein by reference.

FIELD OF INVENTION

The invention relates to a splint for an infant. The invention has particular application to supporting cannulas used on infants, delivered at full term and prematurely, and which require an intravenous supply of medication or fluids.

BACKGROUND TO THE INVENTION

When infants are newly born, they may require intensive medical care which can encompass delivery of medicaments and fluids intravenously. This is particularly true for babies that have not reached full term and are delivered prematurely.

The provision of an intravenous line (IV line) to any human, adult or infant, requires the use of a cannula. This is a thin tube with a hollow needle that is inserted into the vein. For infants, it is common to use veins on the top of the hand/wrist or the ankle.

However, cannulas are not easy to use on infants for a number of reasons.

Firstly, cannulas need to be restrained relative to the body. The most common way of achieving this is through the use of medical tape. However, infants will usually have relatively delicate skin. The adhesive used on medical tape can be quite strong and harsh on the skin so there is a risk of an adverse reaction and in some cases, removal of skin.

Some devices exist that provide an intermediary surface to which a cannula may be secured. An example of such a device is the ARGYLE™ I.V. Support Board, manufactured by COVIDIEN™.

This uses a splint in the form of an elongate piece of foam, sandwiched on one side by a plastic coating and a metal insert. The other side is provided to a layer of loop material. The splint is secured to the arm of the infant with strapping with hook material that is complementary to the loop material used on the splint.

However, this device may still require the use of medical tape to restrain the cannula and/or IV line; the strapping may not be sufficient for this purpose. Thus, there is still potential for medical tape to come into contact with exposed skin. This then has the problem mentioned above, where there is a possibility of the medical tape removing layers of skin when it is removed.

Furthermore, care must be taken to ensure the device is not tightly bound to the infant. This is to avoid the risk that the splint and/or medical tape does not act as a tourniquet, cutting off or otherwise inhibiting circulation to the limb of the infant.

Despite these devices being bulky relative to infants, they are still quite small for an adult to handle. Placing them onto the arm of the infant and then securing the cannula can be very fiddly and delicate work.

As noted above, these devices are large relative to the infant. This is particularly the case when used with prematurely born infants which are smaller than a typical new born. Consequently, it may be difficult to ascertain the position of the infant's fingers when removing the device and/or cannula being supported. Thus, accidental amputation of fingers has been known to occur when using scissors to cut through the tape holding the cannula of the IV in place.

Another issue for infants with cannulas is the relatively uncontrolled movement of their limbs. Being unaware of the cannula, any such movement runs the risk of injury if it comes in contact with the side of the crib or the IV line to which the cannula is attached catches on an object. This can cause movement of the portion of the cannula embedded in the vein and cause considerable damage. This reinforces the need to secure the cannula and/or IV line.

OBJECT OF THE INVENTION

It is an object of the invention to provide an easy-to-use splint for infants, which immobilises a limb of the infant while also being able to support and restrain a cannula and/or intravenous line (IV line) when in use, without damaging the skin.

Alternatively, it is an object to provide a splint which allows for the setting and removal of cannulas and/or IV line with reduced risk of injuring the infant with which the splint is to be used.

Alternatively, it is an object of the invention to at least provide the public with a useful choice.

SUMMARY OF THE INVENTION

According to a first aspect of the invention, there is provided a splint for an infant, wherein the splint includes:
  a body including an insert of a malleable material, wherein the body has a longitudinal axis;
  a first arm extending from an edge of the body in a plane substantially perpendicular to the longitudinal axis; and
  a second arm, spaced apart from the first arm, extending from the edge of the body in a plane substantially perpendicular to the longitudinal axis.

According to another aspect of the invention, there is provided a method of using a splint for an infant, a splint for an infant, wherein the splint includes a body including an insert of a malleable material, wherein the body has a longitudinal axis, the splint also including a first arm extending from an edge of the body in a plane substantially perpendicular to the longitudinal axis, and a second arm, spaced apart from the first arm, extending from the edge of the body in a plane substantially perpendicular to the longitudinal axis, the method including the steps of:
  a) placing a limb of the infant along the longitudinal axis of the body of the splint;
  b) wrapping at least the first arm around the limb; and
  c) securing the first arm to the body with an attachment means.

The invention is a splint for use with infants to secure and retain an intravenous line (IV line) in place with medical tape. Although primarily intended for use on the forearm of an infant, the splint is able to be used on a leg should circumstances dictate it.

At least the majority of the splint should be understood to have a substantially planar form prior to use, i.e. it is substantially flat and is relatively thin. In exemplary embodiments, it may have a thickness of only a few millimetres or thereabouts.

However, it should be appreciated that the splint may not be strictly flat and some minor curvature may be provided. For example, the surface of the splint on which the forearm rests may be slightly curved or recessed to accommodate the typical profile of the forearm of an infant. It will be appreciated that this may mean that a portion of the splint may be slightly thicker than the rest of the splint.

Also, in some embodiments of the invention, an end of the splint may be configured as a sleeve. In use, the hand or feet will be inserted into the sleeve.

In exemplary embodiments of the invention, the splint has a coating of a plastics material.

In particularly preferred embodiments, the coating is a medical grade plastics material which is biocompatible with humans and unlikely to cause irritation of sensitive skin. Preferably, the coating may be silicone or the like. However, this is not intended to be limiting and other types of medical grade plastics material may alternatively be used.

In some embodiments of the present invention, the coating is moulded or otherwise formed with a mesh- or grid-like pattern or texture across some or all of its surface. As it will be appreciated, the splint is designed to be easily trimmed with scissors. The mesh pattern provides some structural integrity to the splint, particularly to its cut edges which would otherwise be at risk of tearing.

In preferred embodiments of the present invention, the body may include a mesh of fabric over which the coating has been applied. This provides some structural integrity to the splint, especially if it has been trimmed for use with an infant.

In some embodiments, the splint is fabricated from two layers of plastics material which form the coating and are brought and bonded together to form a unitary structure. The contact surfaces of the respective layers sandwich or are otherwise moulded around the mesh of fabric. It should be appreciated that reference to a fabric mesh is not meant to be limiting. In some embodiments, the mesh may be a lightweight metal or relatively flexible plastics material.

The splint should be understood to have a body that includes an insert of malleable material. This should be understood to meant that the insert is relatively rigid but is able to be readily deformed upon application of a force. Once the force is removed, the insert remains in a deformed position. This is useful as it can mean that if necessary, the splint may be deformed to accommodate the curvature of the part of the body to which it is applied.

In some embodiments, the coating is applied or moulded around or over the insert during manufacture. However, in other embodiments, where the coating of the splint is formed from two plastic layers brought and bonded together to form a unitary structure, the two layers may sandwich the insert.

In exemplary embodiments, the insert of malleable material is a strip of lightweight metal such as aluminium or brass. Persons skilled in the art will readily appreciated other metals that may be suitable for the intended purpose. Whatever the metal, it is preferable that it be relatively malleable so that it is easy for an adult to bend as required when fitting the splint to an infant. It should also be appreciated that the insert may not form the majority of the body; in exemplary embodiments the coating extends well beyond the edges of the insert.

In some embodiments, where the coating has been applied over a mesh of lightweight metal to enhance structural integrity of the splint, this mesh may serve as the insert of malleable material.

The body has a longitudinal axis; this should be understood to mean that the body has a length dimension which is greater than its width dimension, i.e. the body is elongate. In use, the longitudinal axis is orientated along the length of the arm.

In exemplary embodiments of the invention, the body has a first edge and a second edge defining its width dimension.

Extending laterally from the first edge, i.e. perpendicular to the longitudinal axis of the body of the splint is the first arm.

In exemplary embodiments of the present invention, a second arm, distal to the first arm, also extends from the first edge of the body in a plane substantially perpendicular to the longitudinal axis.

Thus, in exemplary embodiments of the invention, the splint has a pair of arms and these will be understood to be the first arm and the second arm respectively. However, in some embodiments of the invention, additional arms may be present. These may arise from the same edge as the first and second arms or from the opposing edge. In the case of the latter, the additional arms may be intended to overlap or otherwise be connected to the first and second arms in use, and as such may be configured with attachment means to facilitate this. Alternatively, medical tape may be used for this purpose.

In exemplary embodiments of the invention, when in use, the arms wrap around the limb on which the splint is being fitted, such that they substantially fully encircle the limb. This permits the use of an attachment means, such as medical tape to retain the splint in place without having the tape come into contact with the skin of the infant. It will be appreciated that the width of the arms need to be such that there is sufficient surface area to affix the medical tape without it coming into contact with the skin of the infant.

However, in some embodiments of the present invention, the ends of the arms may be configured with hooks corresponding to loops or apertures located on the body. Alternatively, the ends of the arms may be provided with clips, studs or raised lugs that engage with apertures on the body in a snap-lock arrangement. Persons skilled in the art will appreciate that this may be reversed; the apertures may be provided proximate the ends of the arms and it is the body that is configured with the clips or studs.

In exemplary embodiments of the invention, the first and second arms are spatially separated from each other along the first edge of the elongate body.

In exemplary embodiments of the invention, the first arm is proximate one end of the elongate body and the second arm is proximate the other end of the elongate body.

It should be appreciated that in use, the splint is applied to the arm such the end of the body proximate the first arm is closest to the hand/fingers of the infant. Where the splint is being used on the leg, the end of the body proximate the first arm is closest to the foot of the infant.

In exemplary embodiments of the invention, the first and second arms are of substantially similar lengths. It is preferable to make the arms longer than may be required since it is easier to fit a larger splint to an infant (by trimming down the length of the arms) than fitting a splint that is too small.

However, in some embodiments of the invention, as typically the width of the wrist/lower portion of the forearm is less than that of the upper forearm, the first arm of the splint may have a length that is less than that of the second arm (which has to wrap around the wider upper forearm).

In some embodiments of the invention, the first and/or second arm may include an insert of malleable material, such as a strip of lightweight metal such as aluminium or brass. This insert may be integral with the insert of the body, i.e. the insert is one-piece, or alternatively is a separate insert. This allows the arms to be deformed and possible hold the splint in place with minimal or no medical tape.

In some embodiments of the invention, proximate the base of the first arm, near where it meets the first edge of the body, there is provided an aperture or opening through the body. In these embodiments, this is to receive the IV line. The cannula is inserted into the hand or wrist, such that its end extends over the fingers. The IV line extending of the end is then looped under the hand and through the aperture. This retains the line in place.

However, other options for receiving the IV line may include clip-type structures or tabs of hook and loop material such as VELCRO™ may be used instead.

Although the splint is suitable for use with most infants, it may be provided in small, medium, and large sizes so that for particularly little infants, such as prematurely born babies, or large babies, an appropriate splint may still be readily used if desired to avoid or minimise the need to trim the length of the arms.

For example, and without limitation, a splint provided in a medium size may have a body with a length of approximately 80 mm and a width of 25 mm. The length of the first arm, measured from the first edge, is approximately 45 mm while the second arm has a length of 75 mm. Both arms have a width at their base of approximately 20 mm. A splint provided in a small size has dimensions reduced by about 15% while a splint provided as a large size (and which is intended for babies delivered at full term or up to a few months old) has its dimensions increased by 25%. However, as noted these are examples only and are not meant to be limiting.

It also be noted that, apart from the insert, the splint is made from a plastics material and thus is easily trimmed to a desired size with scissors.

The invention offers a number of advantages including but not limited to:
- providing a means of supporting and retaining a cannula and IV line for infants, including those delivered prematurely and requiring medical attention, while still being straightforward to remove if required;
- easily adaptable for infants of different sizes;
- may be used on both arms and legs of infants as required;
- is configured to avoid the need for medical tape to come into contact with the skin of the infant.

Further aspects of the invention, which should be considered in all its novel aspects, will become apparent to those skilled in the art upon reading of the following description which provides at least one example of a practical application of the invention.

BRIEF DESCRIPTION OF THE DRAWINGS

One or more embodiments of the invention will be described below by way of example only, and without intending to be limiting, with reference to the following drawings, in which.

BEST MODES FOR CARRYING OUT THE INVENTION

Figure 1:
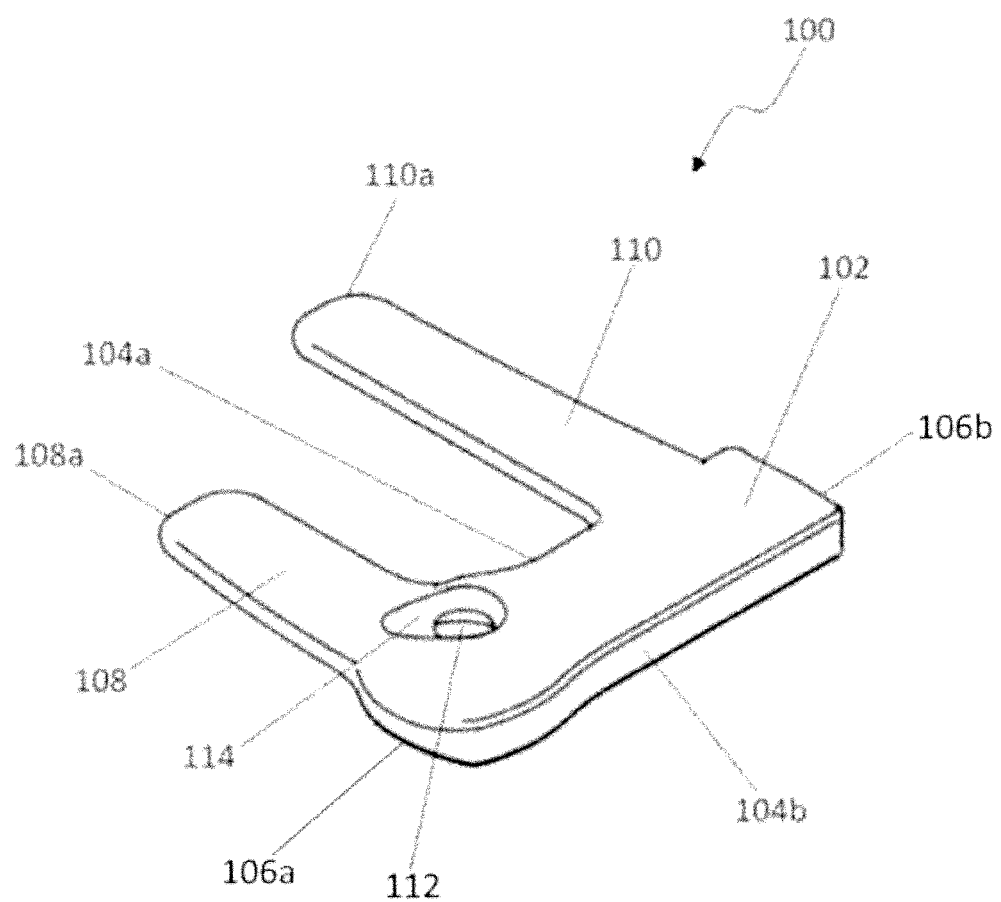
FIG. 1 is a perspective view of one embodiment of the invention.

The invention in the form of a splint (generally indicated by arrow 100) for an infant (not shown) is illustrated in a perspective view in FIG. 1.

The splint (100) has a body (102). In use, this would be orientated along the arm of the infant (not shown) with which the invention is to be used. The body has a first (104a) and second edge (104b), defining the width of the body, and a first (106a) and second end (106b), defining the length of the body. As can be seen, the body is elongate and its length defines the longitudinal axis of the splint.

The first end (106a) of the body (102) is slightly widened relative to the second end (106b); this is to better accommodate the hand (or foot as the case may be) of the infant when the splint (100) is being used.

Extending perpendicularly from the first edge (104a) of the body (102) are a pair of arms; these are the first (108) and second (110) arms. In use, these would wrap around the arm of the infant (not shown) until at the least the free ends (108a, 110a) of each arm contacts the body (102). This provides a continuous surface over which medical tape (not shown) can be applied to secure the splint to the forearm of the infant. This avoids the need for the medical tape to come into contact with the skin of the infant, thereby reducing or eliminating the risk that layers of skin may be removed as the medical tape is peeled off.

The second arm (110) is longer than the first arm (108). This is to compensate for the greater circumference of the upper portion of the forearm of the infant (not shown) relative to the lower portion. In use, the first arm of the splint (100) is likely to be wrapped around the hand and/or wrist of the infant.

As can be seen, the splint (100) is substantially flat and planar when not in use. However, although not shown here, a slight depression may be provided along the length of the body (102). This forms a natural surface that accommodates the curvature of the infant's forearm in use.

For biocompatibility, the splint (100) is coated with a medical grade plastics material such as silicone or the like. Such material is able to be stretched if need be, for example, for a tight fit onto the forearm (not shown) and is easily cut. This allows the length of the arms (108, 110) to be trimmed to improve the fit of the splint and/or better secure the cannula (not shown). To reduce the risk of any cut edges being torn, which may be a concern for softer plastics material such as silicone, the coating may be moulded with a mesh-like texture (not illustrated) which provides some structural integrity. Alternatively, in some embodiments not shown here, the coating may be moulded over or around a fabric mesh to achieve the same effect.

In the embodiment of FIG. 1, the body (102) of the splint (100) is reinforced internally with an insert (not visible) of a malleable metal, such as a strip of aluminium or brass. The width of the insert is less than the width of the body, as defined by its first (104a) and second edges (104b); this allows the portions of the splint to either side of the insert, i.e. the portions that are only plastics material, to be trimmed with scissors or the like if desired. The coating of the splint is applied over this insert during manufacture.

This provides some structural integrity to the splint (100) and makes it easier to handle. It also means that if necessary, the splint is easily malleable to conform to the shape of the arm or leg of the infant (not shown). This can be helpful if, for example, the wrist needs to be held at an angle. Once in the desired configuration, the insert ensures that the wrist remains this way until the splint is removed.

In embodiments not illustrated here, the surfaces of the arms (108, 110) that face inwards in use may textured to enhance the grip of the arms on the skin of the infant (not shown). The reverse surfaces of the arms, which face outwards in use could include patterns or textures (not shown) for an aesthetically pleasing appearance and, as noted above, for increased structural integrity. However, these could just as easily carry advertising or medical information pertaining to the infant.

The splint (100) also includes an aperture or opening (112) proximate the first edge (104*a*) of the body (102), near the first arm (108). In use, this is to accommodate the cannula of the IV line (not shown) being supported with the invention. The opening is within a depression (114), and this helps with aligning the cannula/IV line.

Figure 2A:
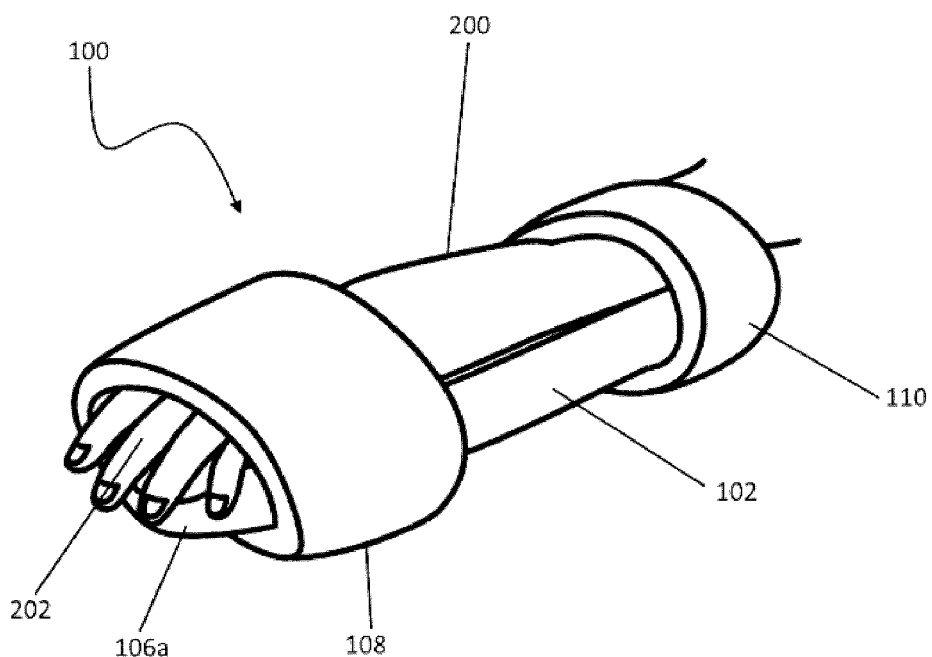
FIG. 2A is a perspective view of the embodiment of FIG. 1 attached to the arm of an infant.

Turning now to FIG. 2A, this shows the splint (100) in use on the forearm (200) of an infant. As can be seen, the forearm rests on the body (102) of the splint with the arms (108, 110) wrapped around it.

Although not shown here, adhesive tape can be wrapped over the exposed surfaces of the arms (108, 110) to hold the splint (100) in place and the arms provide two distinct and separate points for securing the splint. The adhesive tape sits well proud of the arm (200) and fingers (202) of the infant, avoiding contact with the skin. This also reduces the risk that the fingers would be inadvertently amputated when cutting through the medical tape in order to remove the splint.

The cannula (not shown) extends forward from the first end (106*a*) of the body (102) of the splint (100) and its IV line (not shown) is tucked under the hand and passes through the aperture (not visible) in the body. This helps to securely retain the IV line even if the infant moves their arm (200).

Figure 2B:
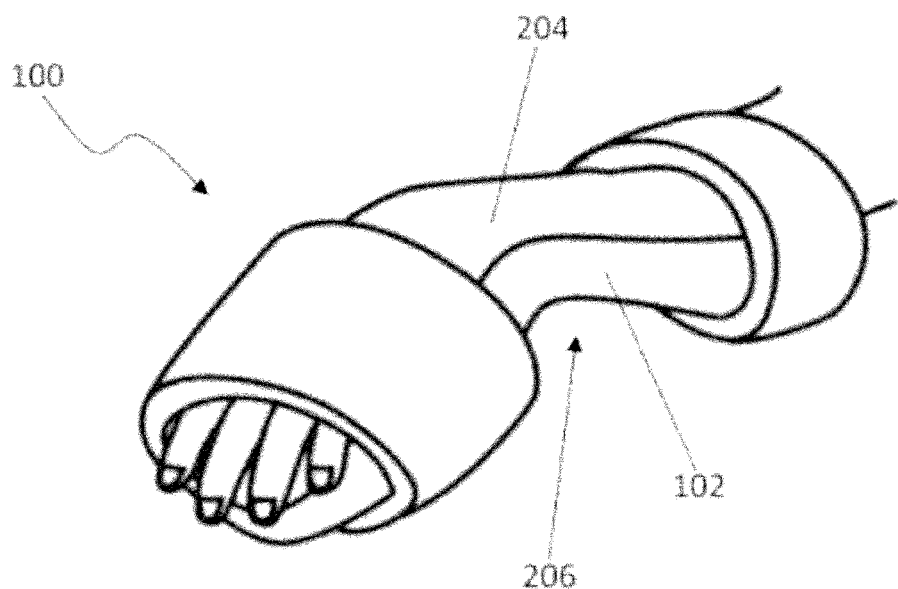
FIG. 2B is a perspective view of the embodiment of FIG. 1 attached to the arm of an infant in an alternative configuration.

The general orientation of the splint (100) can be adapted to allow for different arm orientations as shown in FIG. 2B. This is due to the malleability of the insert (not visible) within the body (102). This allows for the body to bent along its transverse axis, i.e. perpendicular to the longitudinal axis of the body.

In the illustrated example, it will be seen that the body (102) of the splint (100) has been bent such that it presents the upper side (204) of the hand for easier inspection. It also defines a recess (206) under the body which could allow for the cannula and/or other medical paraphernalia (not shown) to be more discreetly accommodated in use.

Figure 3:
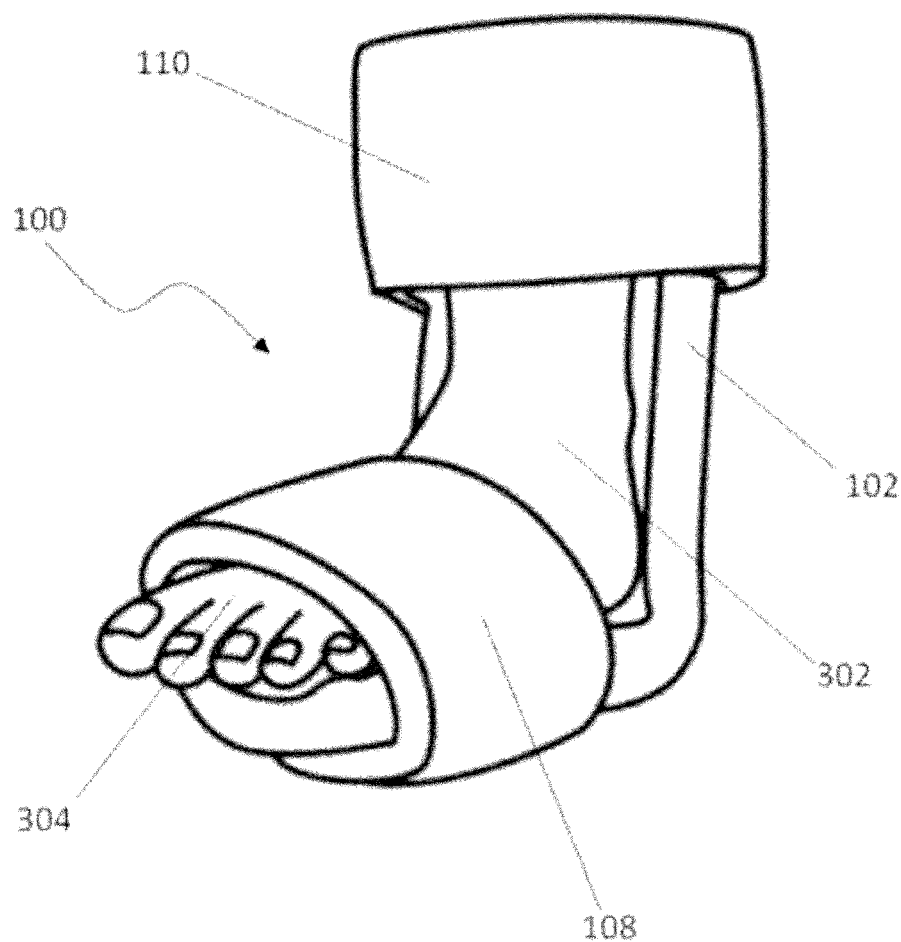
FIG. 3 is a perspective view of the embodiment of FIG. 1 attached to the leg of an infant.

Although intended mainly for use on the forearm, it is also possible to use the splint (100) on the lower part (300) of the leg, as shown in FIG. 3. Here it can be seen that the body (102) has been bent to substantially 90° to better conform to the curvature of the heel (302) of the foot (304). The first arm (108) is wrapped around the foot while the second arm (110) is wrapped around the lower leg.

Figure 4:
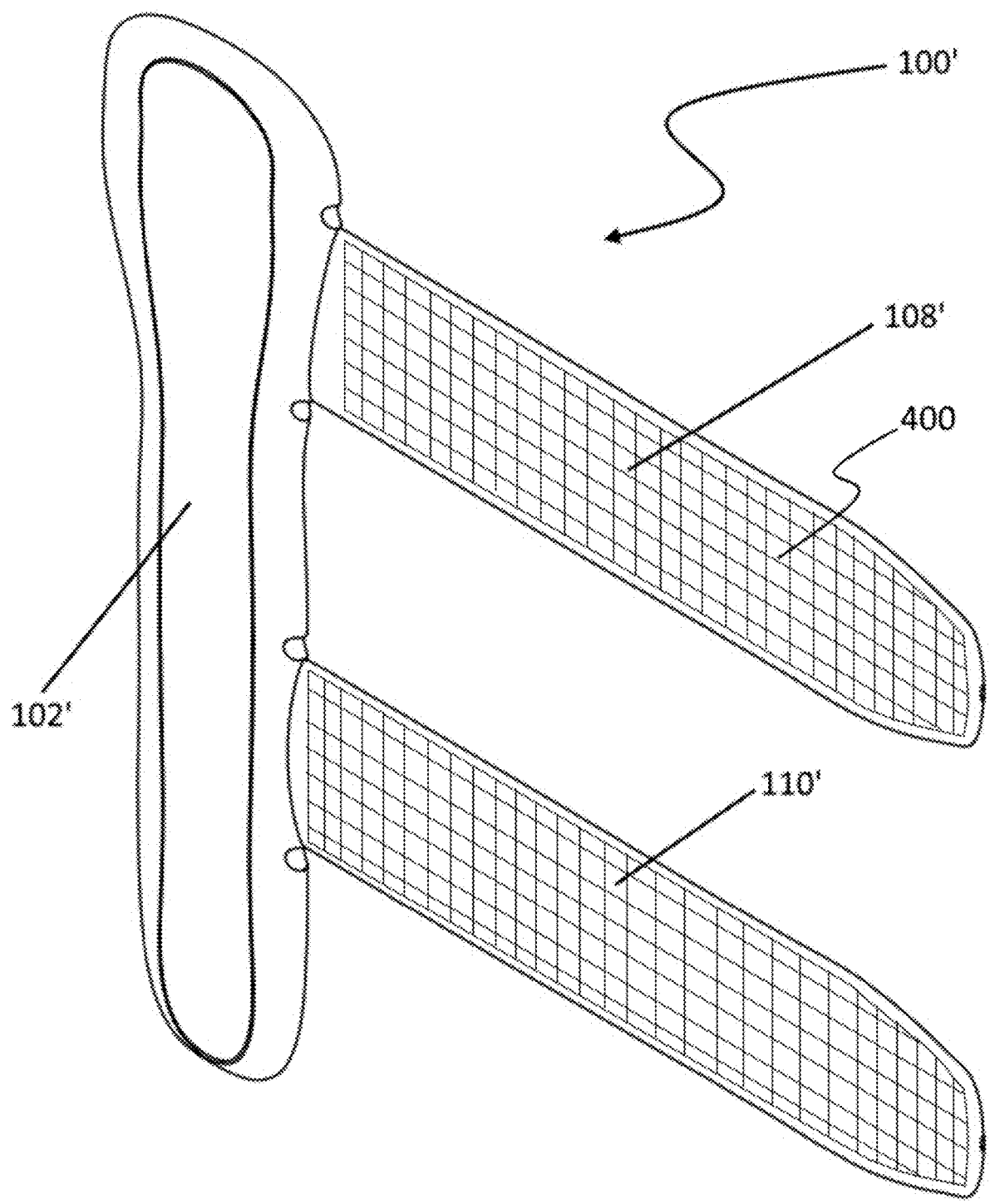
FIG. 4 is a perspective view of a further embodiment of the invention.

An alternative embodiment of the splint (100') is shown in FIG. 4. As will be seen, there is substantial identity between the embodiment of FIG. 1 and that shown in FIG. 4. However, it will be seen that in FIG. 4, the arms (108' and 110') are substantially equal in length and are of slightly reduced thickness relative to the body (102') of the splint. The reduced thickness means that the arms are much easier to articulate.

Having the arms (108', 110') of substantially equal length allows greater capacity for customisation of the splint (100'), particularly in respect of the first arm (108'), which generally corresponds to the wrist in use. Any excess can be trimmed off if needed. The coating on the first arm includes a grid-like pattern or texture (400) on its surface to provide some structural integrity to any cut edges. Another difference is the absence of an aperture in the body (102') of the splint (100'); this simplifies manufacture. However this does mean the splint itself has no structural features that may be used to retain an IV line or cannula (not shown).

Figure 5:
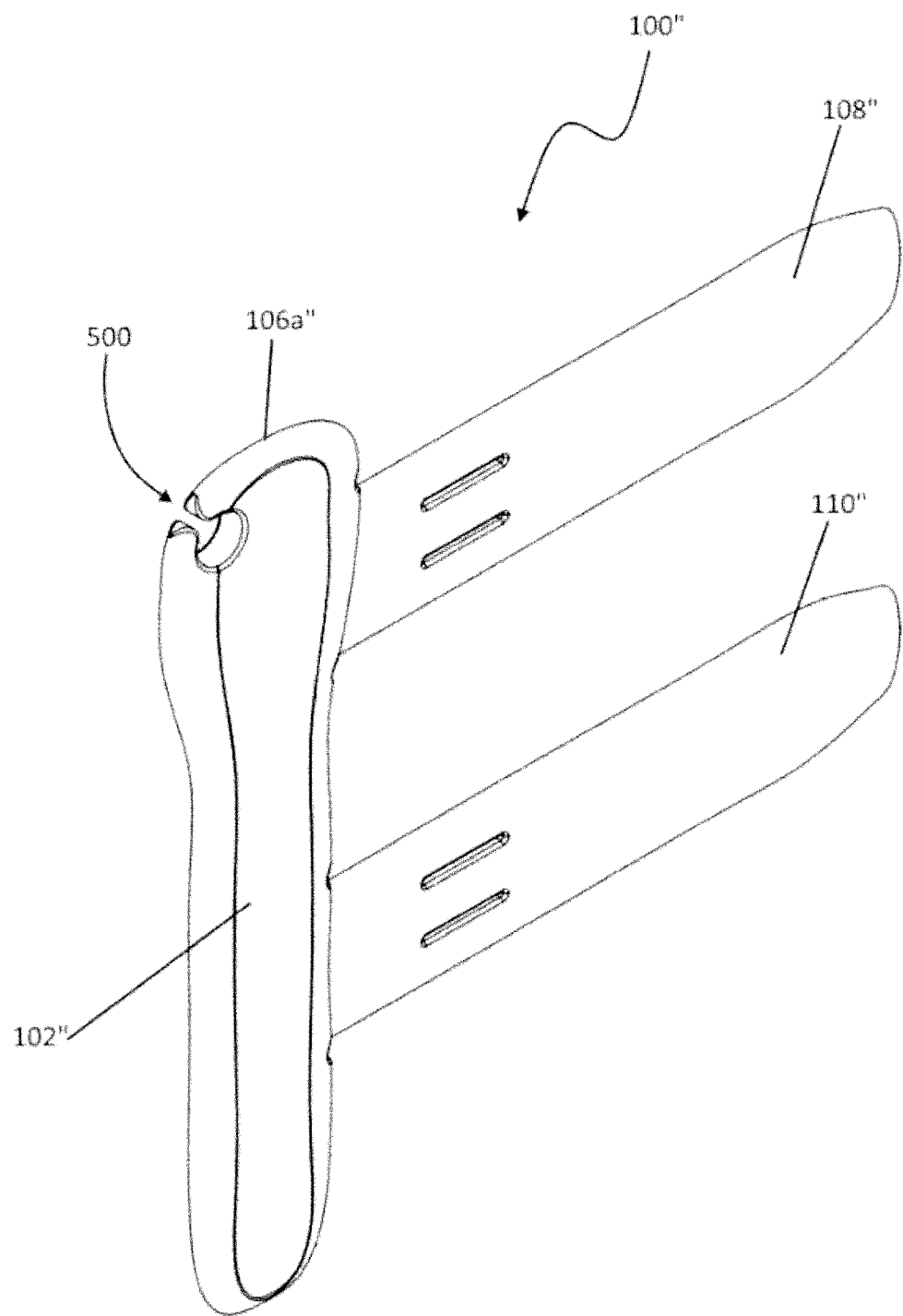
FIG. 5 is a perspective view of yet another embodiment of the invention.

A further embodiment of the splint (100") is shown in FIG. 5. This is substantially similar to the embodiment of FIG. 4 but at the first end (106*a*") of the body (102") an open recess (500) is provided.

This recess acts as a clip for receiving an IV line or cannula (not shown). Furthermore, making it an open recess, i.e. forming it as part of the perimeter of the body makes it easier for the IV line or cannula to be inserted even while the splint (100") is being worn.

In contrast, in the splint (100) of FIG. 1, where the aperture (114) is positioned inwards of the body (102) such that it does not open onto the perimeter of the body, the IV line or cannula (not shown) must be threaded through the aperture. This may be difficult to due while the splint is being worn.

As with previous embodiments, the splint (100") of FIG. 5 includes a malleable insert of a light metal. Although not visible in this embodiment, the insert may be in the form of a mesh of a light metal. This not confers the splint with the ability to retain a deformed position to conform to the limb with which it is being used but also provides the body (102") with some structural integrity should it need to be trimmed to size. Mesh may also be used in the first and second arms (108", 110") for the same reason.

Unless the context clearly requires otherwise, throughout the description and the claims, the words "comprise", "comprising", and the like, are to be construed in an inclusive sense as opposed to an exclusive or exhaustive sense, that is to say, in the sense of "including, but not limited to".

The entire disclosures of all applications, patents and publications cited above, if any, are herein incorporated by reference.

Reference to any prior art in this specification is not, and should not be taken as, an acknowledgement or any form of suggestion that that prior art forms part of the common general knowledge in the field of endeavour in any country in the world.

The invention may also be said broadly to consist in the parts, elements and features referred to or indicated in the specification of the application, individually or collectively, in any or all combinations of two or more of said parts, elements or features.

Where in the foregoing description reference has been made to integers or components having known equivalents thereof, those integers are herein incorporated as if individually set forth.

It should be noted that various changes and modifications to the presently preferred embodiments described herein will be apparent to those skilled in the art. Such changes and modifications may be made without departing from the spirit and scope of the invention as defined in the appended claims and without diminishing its attendant advantages. It is therefore intended that such changes and modifications be included within the present invention.

Figure 6:
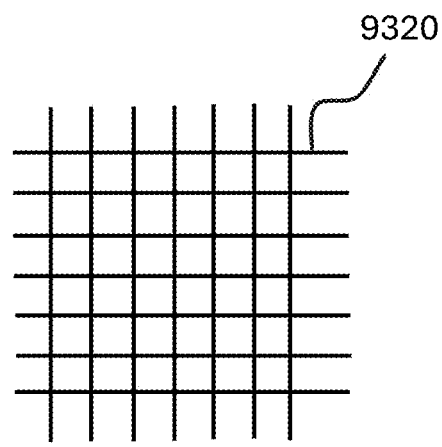
FIG. 6 is a view of yet another embodiment of the invention.

In an embodiment, the splint includes a surface formed with a grid-like pattern or texture (9320) as seen in FIG. 6.

The claims defining the invention are:

1. A splint for an infant, wherein the splint includes:
   a body, including an insert of a malleable material, wherein the body has a longitudinal axis;

a first arm extending from an edge of the body in a plane substantially perpendicular to the longitudinal axis, wherein the first arm includes an attachment surface; and a second arm, spaced apart from the first arm, extending from the edge of the body in a plane substantially perpendicular to the longitudinal axis;

wherein the body, the first arm and the second arm include a mesh of fabric;

and wherein the entire splint is coated by a medical grade plastics material.

2. The splint as claimed in claim 1, wherein the insert of malleable material is a strip of lightweight metal.

3. The splint as claimed in claim 1, wherein the insert of malleable material is a mesh of lightweight metal.

4. The splint as claimed in claim 1, wherein the mesh of fabric is a flexible plastics material.

5. The splint as claimed in claim 1, wherein the splint includes a surface formed with a grid-like pattern or texture.

6. The splint as claimed in claim 1, wherein the first and second arms are of substantially similar lengths.

7. The splint as claimed in claim 1, wherein the first and/or second arm includes an insert of malleable material.

8. The splint as claimed in claim 7, wherein the insert of the first and/or second arm is integral with the insert of the body.

9. The splint as claimed in claim 7, wherein the insert of the first and/or second arm is a strip or mesh of a lightweight metal.

10. The splint as claimed in claim 1, wherein the body is configured to receive an IV line or IV cannula.

11. The splint as claimed in claim 1, wherein at least a majority of the splint has a substantially planar form prior to use.

12. The splint as claimed in claim 1, wherein the body includes an end, and wherein the end is configured as a sleeve.

13. The splint as claimed in claim 1, wherein the splint for an infant includes an outer profile that has a curved surface that lies on a second plane that parallel to the longitudinal axis.

14. The splint as claimed in claim 1, wherein with respect to respective sides of a second plane that is normal to the longitudinal axis, the body of the splint for an infant is asymmetrical.

15. The splint as claimed in claim 1, wherein the first arm of the splint for an infant has a curved end.

16. A method of using a splint for an infant, wherein the splint includes:

a body, including an insert of a malleable material, wherein the body has a longitudinal axis;

a first arm extending from an edge of the body in a plane substantially perpendicular to the longitudinal axis, wherein the first arm includes an attachment surface; and a second arm, spaced apart from the first arm, extending from the edge of the body in a plane substantially perpendicular to the longitudinal axis;

wherein the body, the first arm and the second arm include a mesh of fabric;

and wherein the entire splint is coated by a medical grade plastics material, the method including the steps of:

a) placing a limb of the infant along the longitudinal axis of the body of the splint;

b) wrapping at least the first arm around the limb; and c) securing the first arm to the body.

17. The method as claimed in claim 16, wherein the limb is the arm and/or wrist of the infant.

18. The method as claimed in claim 16, wherein the limb is the leg and/or ankle of the infant.

19. The method as claimed in claim 16, wherein the first arm is secured to the body by applying a strip of adhesive tape to the attachment surface.

20. The method as claimed in claim 16, wherein the first arm and/or the second arm is secured to the body by a fastener structure provided to an end of the first and first and/or second arms.

* * * * *